(12) United States Patent
Arora et al.

(10) Patent No.: US 8,877,947 B2
(45) Date of Patent: Nov. 4, 2014

(54) PROCESS FOR PREPARATION OF SUBSTANTIALLY PURE FOSAMPRENAVIR CALCIUM AND ITS INTERMEDIATES

(75) Inventors: Surinder Kumar Arora, Pune (IN); Samir Shanteshwar Shabade, Pune (IN); Gaurav Kumar, Pune (IN); Purna Chandra Ray, Pune (IN); Girij Pal Singh, Pune (IN)

(73) Assignee: Lupin Limited (IN)

( * ) Notice: Subject to any disclaimer, the term of this patent is extended or adjusted under 35 U.S.C. 154(b) by 0 days.

(21) Appl. No.: 13/822,197

(22) PCT Filed: Sep. 5, 2011

(86) PCT No.: PCT/IB2011/002045
§ 371 (c)(1),
(2), (4) Date: Mar. 11, 2013

(87) PCT Pub. No.: WO2012/032389
PCT Pub. Date: Mar. 15, 2012

(65) Prior Publication Data
US 2013/0174651 A1 Jul. 11, 2013

(30) Foreign Application Priority Data
Sep. 10, 2010 (IN) .......................... 1006/KOL/2010

(51) Int. Cl.
*C07D 307/20* (2006.01)
*C07F 9/06* (2006.01)
*G01N 30/16* (2006.01)
*C07D 405/12* (2006.01)

(52) U.S. Cl.
CPC .............. *C07D 307/20* (2013.01); *G01N 30/16* (2013.01); *C07D 405/12* (2013.01)
USPC .......................................... 549/222; 549/218

(58) Field of Classification Search
CPC ................................ C07D 307/20; C07F 9/06
USPC .................................................. 549/218, 222
See application file for complete search history.

(56) References Cited

U.S. PATENT DOCUMENTS 6,436,989 B1 * 8/2002 Hale et al. ...................... 514/81

FOREIGN PATENT DOCUMENTS

WO 9405639 A1 3/1994

OTHER PUBLICATIONS

B. Moon Kim et al., "Synthesis of a Chiral Azirindine Derivative as a Versatile Intermediate for HIV Protease Inhibitors," Organic Letters, 2001, vol. 3, No. 15, pp. 2349-2351.
International Search Report and Written Opinion; International Application No. PCT/IB2011/002045; International Filing Date: Sep. 5, 2011; Date of Mailing: Mar. 23, 2012; 16 pages.
L.A. Sorbera et al., "Fosamprenavir," Drugs of the Future 2001, 26(3); 224-231, XP009001334.
Victor Ekhato et al., "Isotope labeled HEA/HEE moiety in the synthesis of labeled HIV-protease inhibitors—Part II," J. Label Compd Radiopharm, 2005; 48; 179-193.

* cited by examiner

*Primary Examiner* — Golam M M Shameem
(74) *Attorney, Agent, or Firm* — Cantor Colburn LLP

(57) ABSTRACT

The present invention relates to fosamprenavir calcium (Ia) substantially free of isomer impurity, (3R)tetrahydro-3-furanyl(1S,2R)-3-[[(4-aminophenyl)sulfonyl](isobutyl)amino]-1-benzyl-2-(phosphonooxy)propyl carbamate (Ib), and its process for preparation thereof. The present invention also provides fosamprenavir calcium intermediate, (S)-3-tetrahydrofuranyl-N-succinimidyl carbonate (IIa) substantially free of (R)-3-tetrahydrofuranylsuccinimidyl carbonate (IIb) and its process for preparation thereof.

7 Claims, No Drawings

PROCESS FOR PREPARATION OF SUBSTANTIALLY PURE FOSAMPRENAVIR CALCIUM AND ITS INTERMEDIATES

This is a U.S. national stage application of International Application No. PCT/IB2011/002045, filed on 5 Sep. 2011. Priority under 35 U.S.C. §119(a) and 35 U.S.C. §365(b) is claimed from Indian Application No. 1006/KOL/2010, filed 10 Sep. 2010, the disclosure of which is also incorporated herein by reference.

FIELD OF INVENTION

The present invention relates to fosamprenavir calcium (Ia) substantially free of isomer impurity, (3R)tetrahydro-3-furanyl(1S,2R)-3-[[(4-aminophenyl)sulfonyl](isobutyl)amino]-1-benzyl-2-(phosphonooxy)propyl carbamate (Ib), and its process for preparation thereof.

BACKGROUND OF THE INVENTION

Fosamprenavir calcium has HIV aspartyl protease inhibitory activity and is particularly well suited for inhibiting HIV-1 and HIV-2 viruses; it is chemically known as calcium (3S)tetrahydro-3-furanyl(1S,2R)-3-[[(4-aminophenyl)sulfonyl](isobutyl)amino]-1-benzyl-2-(phosphonooxy)propyl carbamate and represented by formula Ia.

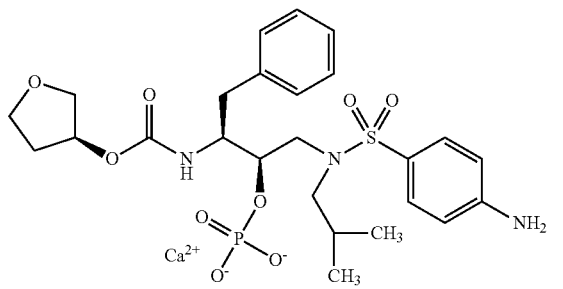

There are very few references available in the literature for preparation of fosamprenavir and its intermediates. U.S. Pat. No. 5,585,397 provides process for preparation of fosamprenavir intermediate (IV), as depicted in scheme 1, wherein it is purified using silica gel chromatography, however it does not provide any purity data. Purification by column chromatography is not suitable on commercial scale, since it is time consuming, requires large volume of solvents and is very much laborious.

Scheme 1: Process for preparation of fosamprenavir intermediate (IV) as given in U.S. Pat. No. 5,585,397

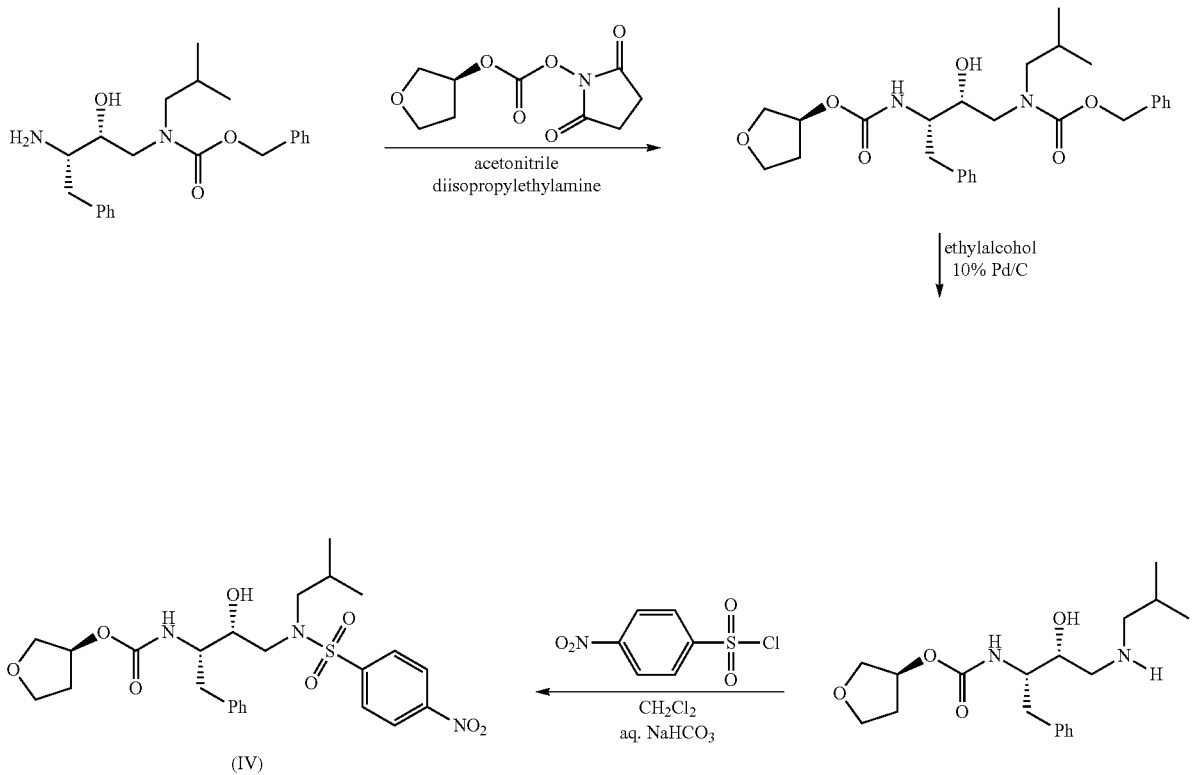

Another U.S. Pat. No. 6,281,367, provides process for preparation of fosamprenavir intermediate (IV) as depicted in scheme 2, but it does not provide any method for purification of compound (IV).

Scheme 2: Process for preparation of fosamprenavir intermediate (VI) as given in U.S. Pat. No. 6,281,367

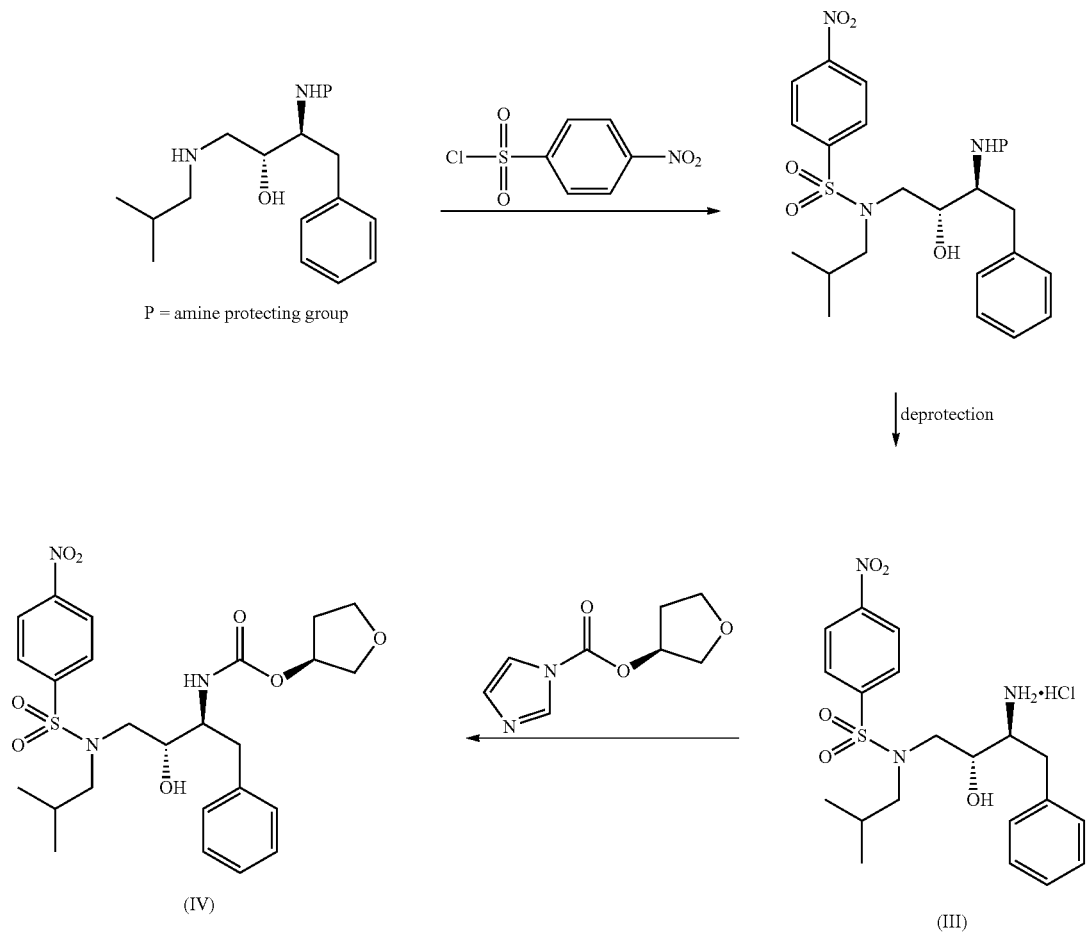

The U.S. Pat. No. 6,514,953 provides process for preparation of fosamprenvair calcium (Ia) utilizing compound (IV), as depicted in Scheme 3, however it does not provide purity of fosamprenavir calcium (Ia) or the intermediates thereof.

Scheme 3: Process for preparation of fosamprenavir Calcium (Ia) as given in U.S. Pat. No. 6,514,953

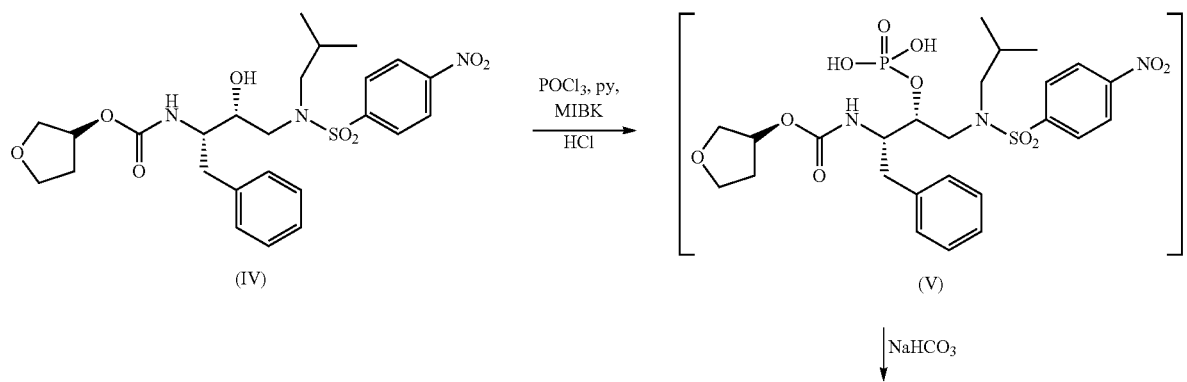

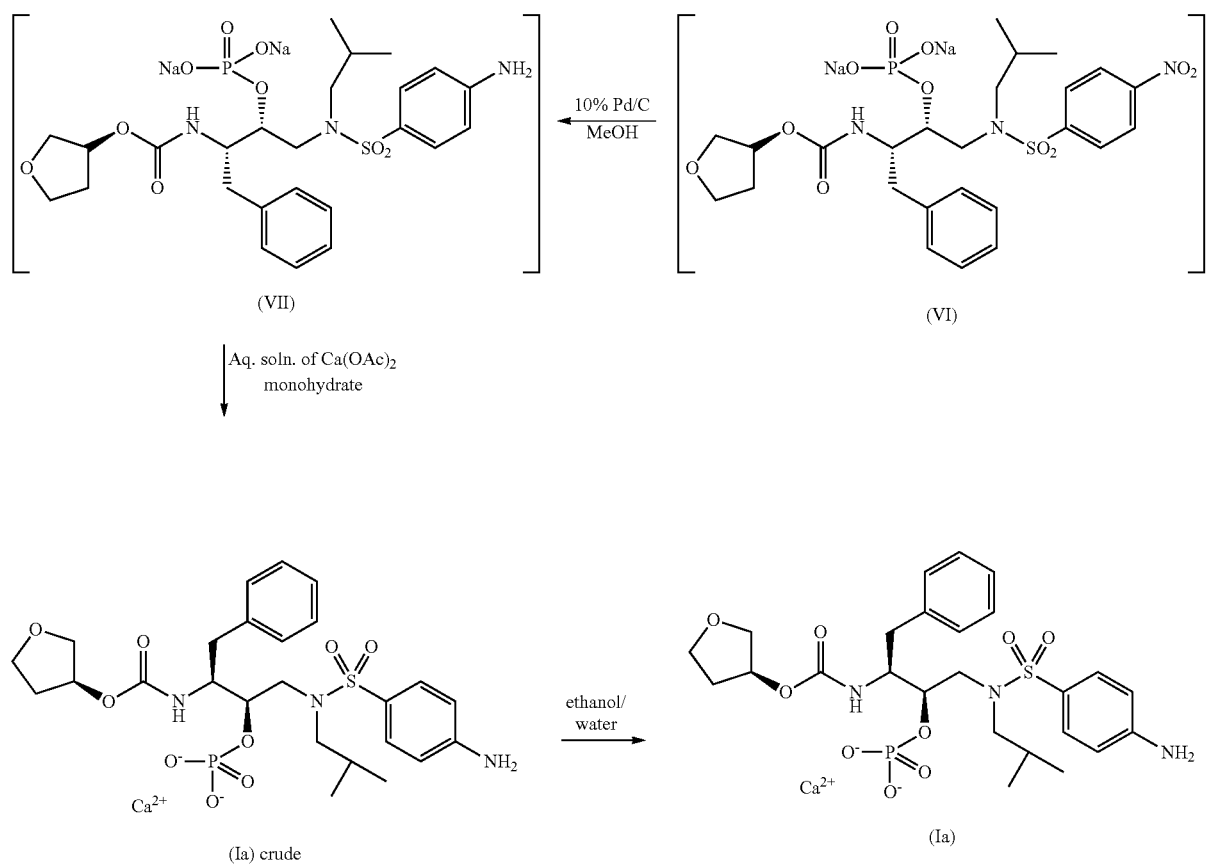
Another U.S. Pat. No. 6,436,989, which is product patent for fosamprenavir salts, provide process for preparation of fosamprenavir sodium salt (VII) from compound (IV) as depicted in Scheme 4:
Scheme 4: Process for preparation of fosamprenavir sodium (VII) as given in U.S. Pat. No. 6,436,989.
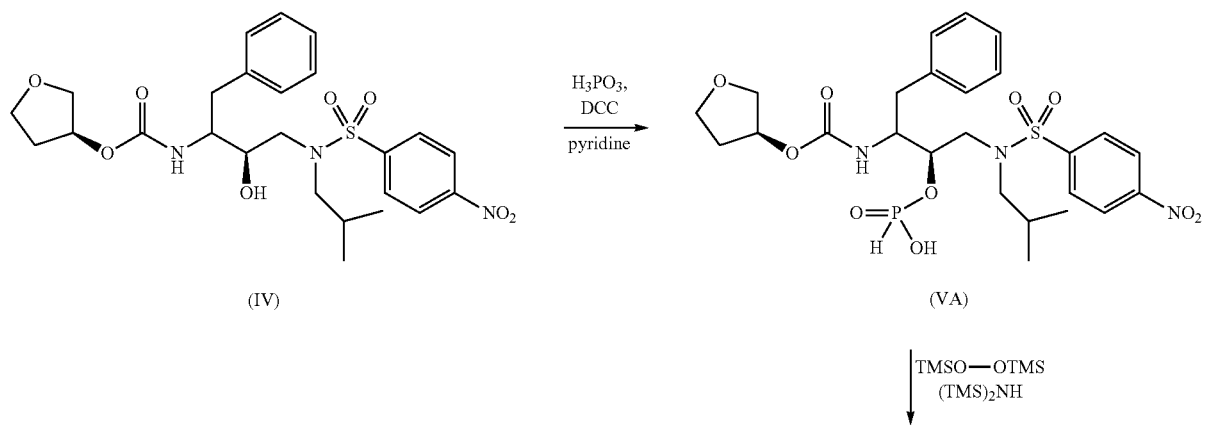

-continued

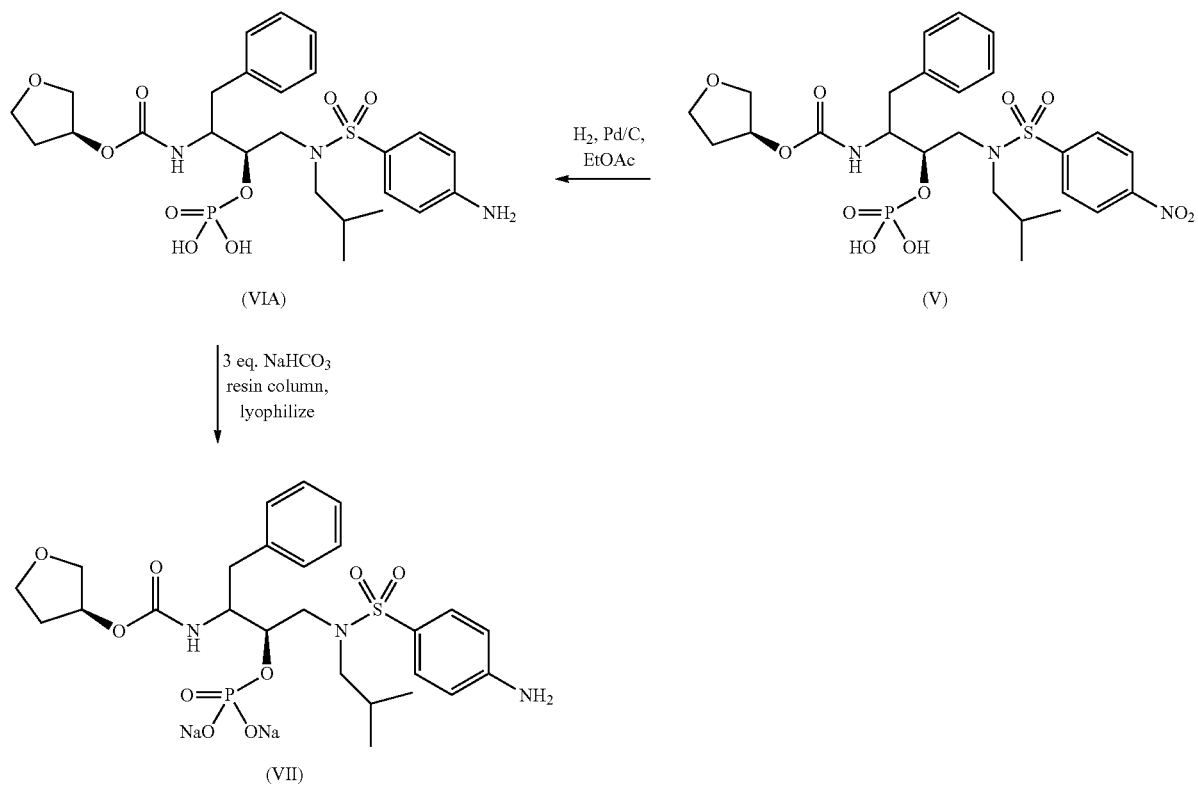

U.S. Pat. No. 6,436,989 provides compound (V) and (VIA) with an HPLC purity of 90% and 92% respectively, however purity of fosamprenavir sodium salt (VII) is not mentioned. This patent provides fosmaprenavir salt intermediates with very low HPLC purity.

The prior art literature describes synthesis of fosamprenavir calcium and its intermediates and like any synthetic compound, fosmaprenavir calcium can contain number of impurities from various source like starting material, reaction by-products, degradation, isomeric impurities etc. The prior art documents for fosamprenavir calcium does not provide any information for the impurities that may have been formed from the various synthetic processes provided therein.

Fosamprenavir calcium i.e. calcium (3S)tetrahydro-3-furanyl(1S,2R)-3-[[(4-aminophenyl)sulfonyl](isobutyl)amino]-1-benzyl-2-(phosphonooxy)propyl carbamate (Ia), is a chiral substrate containing three asymmetrical carbon centre resulting into eight stereoisomers.

Different isomers of a chiral drug molecule bind differently to target receptors, one isomer of a drug may have a desired beneficial effect while the other may cause serious and undesired side effects or sometimes even beneficial but entirely different effects, hence in the drug molecules the effective isomer is preferred in pure form, free of other undesired isomers, thus fosamprenavir calcium free of its other stereoisomer would always be preferred.

The methods described above for preparation of fosamprenavir does not describe suitable methods to minimize formation of R-isomer impurity (Ib)

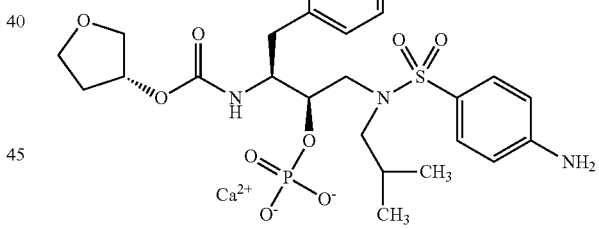

One of the approach to minimize R-isomer impurity (Ib) is to use highly pure intermediate (S)-3-tetrahydrofuranyl-N-succinimidyl carbonate (IIa), in the synthesis of fosamprenavir.

U.S. Pat. No. 5,585,397 provides process for preparation of N-succinimidlyl-(S)-3-tetrahydrofuryl carbonate (IIa), however it does not provide any method for purification neither does it provide any purity data for the same.

The PCT application WO 94/18192 provides process for preparation (S)-3-tetrahydrofuranyl-N-succinimidyl carbonate (IIa) as depicted in scheme 5. The application discloses recrystallization of compound (IIa) from EtOAc/hexane. At our hands, crystallization of compound (IIa) from ethyl acetate/hexane provided compound (IIa) containing the intermediate R-isomer impurity compound (IIb) upto 0.37% area percentage of HPLC, which is not suitable for its use in the synthesis of fosamprenavir substantially free of R-isomer impurity (Ib).

Scheme 5: process for preparation of (S)-3-tetrahydrofuranyl-N-succinimidyl carbonate

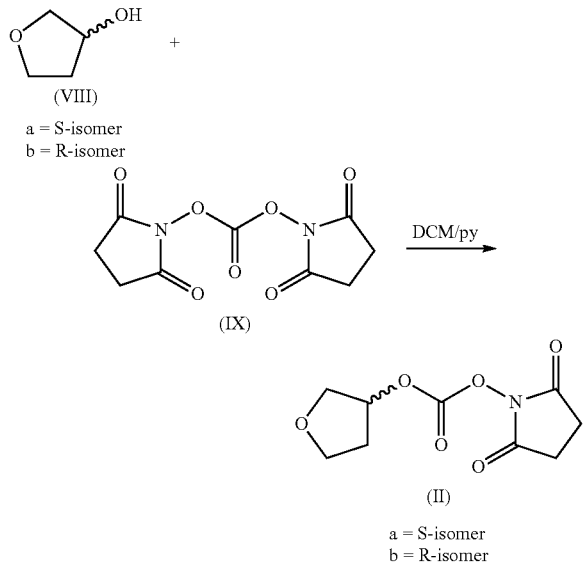

a = S-isomer
b = R-isomer

Commercially available (S)-3-tetrahydrofuranol (VIIIa) contains upto 5% area percentage of HPLC of (R)-3-tetrahydrofuranyl (VIIIb), which on reaction with N,N-disuccinimidyl carbonate (IX) results in (S)-3-tetrahydro furanyl-N-succinimidyl carbonate (IIa) containing upto 2.5% area percentage of HPLC of the R-isomer impurity, (R)-3-tetrahydrofuranyl-N-succinimidyl carbonate (IIb). This impure (S)-3-tetrahydrofuranyl-N-succinimidyl carbonate (IIa) when converted to fosamprenavir calcium (Ia) by series of reaction, results into fosamprenavir calcium containing upto 2.0% area percentage of HPLC of (3R)tetrahydro-3-furanyl(1S,2R)-3-[[(4-aminophenyl)sulfonyl](isobutyl)amino]-1-benzyl-2-(phosphonooxy)propyl carbamate (Ib), which is undesired isomer of fosamprenavir calcium.

Impurities of any form are undesirable in the active pharmaceutical product since it may have adverse effect on the patient to be treated.

The purity of API produced is clearly a necessary condition for commercialization. The impurities produced in the manufacturing process must be limited to very small amount and are preferred to be substantially absent. The ICH Q7A guidance for API manufacturers requires that process impurities must be maintained below set limits utilizing various parameters. In the United States the Food and Drug Administration guidelines, would mostly limit the amount of impurities present in the API, similarly in other countries the impurity levels would be defined in their respective pharmacopeias.

Fosamprenavir calcium is not a pharmacopeial product at present and the guidelines for the amount of impurities is not provided, however substantially pure fosamprenavir calcium would always be preferred. The objective to the present invention is directed to the same.

SUMMARY OF THE INVENTION

The present invention provides process for preparation of fosamprenavir calcium (Ia) substantially free of R-isomer impurity (Ib) comprising:
a) analyzing the level of intermediate R-isomer impurity (IIb) in a sample of (S)-3-tetrahydrofuranyl-N-succinimidyl carbonate (IIa);
b) selecting a sample of (S)-3-tetrahydro furanyl-N-succinimidyl carbonate (IIa) containing less than 0.2% area percentage of HPLC of intermediate R-isomer impurity (IIb);
c) reacting said (S)-3-tetrahydro furanyl-N-succinimidyl carbonate (IIa) with (2R,3S)—N-(3-amino-2-hydroxy-4-phenylbutyl)-N-isobutyl-4-nitrobenzene sulphonamide (III) to obtain (3S)-tetrahydro-3-furanyl N-[(1S,2R)-1-benzyl-2-hydroxy-3-(N-isobutyl-4-nitrobenzene sulphonamido)propyl]carbamate (IV); and
d) conversion of compound (IV) to fosamprenavir calcium (Ia).

The present invention also provides fosamprenavir calcium intermediate, (S)-3-tetrahydrofuranyl-N-succinimidyl carbonate (IIa) substantially free of (R)-3-tetrahydrofuranyl-succinimidyl carbonate (IIb) and its process for preparation thereof.

DETAILED DESCRIPTION OF THE INVENTION

The present invention provides fosamprenavir calcium substantially free of (3R)tetrahydro-3-furanyl(1S,2R)-3-[[(4-aminophenyl)sulfonyl](isobutyl)amino]-1-benzyl-2-(phosphonooxy)propyl carbamate (Ib). Compound (Ib) is referred as "R-isomer impurity" herein.

Fosamprenavir calcium (Ia) substantially free of R-isomer impurity (Ib) refers to compound (Ia) with less than 0.2%, preferably less than 0.15%, more preferably less than 0.1%, area percentage of HPLC of R-isomer impurity.

Another embodiment of the present invention provides process for preparation of fosamprenavir calcium (Ia) substantially free of R-isomer impurity (Ib) comprising:
a) analyzing the level of intermediate R-isomer impurity (IIb) in a sample of (S)-3-tetrahydrofuranyl-N-succinimidyl carbonate (IIa);
b) selecting a sample of (S)-3-tetrahydro furanyl-N-succinimidyl carbonate (IIa) containing less than 0.2% area percentage of HPLC of intermediate R-isomer impurity (IIb);
c) reacting said (S)-3-tetrahydro furanyl-N-succinimidyl carbonate (IIa) with (2R,3S)—N-(3-amino-2-hydroxy-4-phenylbutyl)-N-isobutyl-4-nitrobenzene sulphonamide (III) to obtain (3S)-tetrahydro-3-furanyl N-[(1S,2R)-1-benzyl-2-hydroxy-3-(N-isobutyl-4-nitrobenzene sulphonamido)propyl]carbamate (IV); and
d) conversion of compound (IV) to fosamprenavir calcium (Ia).

In yet another embodiment the present invention provides fosamprenavir calcium intermediate, (S)-3-tetrahydro furanyl-N-succinimidyl carbonate (IIa), substantially free of (R)-3-tetrahydrofuranylsuccinimidyl carbonate (IIb).

(S)-3-tetrahydrofuranyl-N-succinimidyl carbonate (IIa) is prepared from commercially available (S)-3-tetrahydrofuranol, by the methods known in art, such as WO 94/18192 and subjected to purification.

The present invention also provides process for preparation of intermediate, (S)-3-tetrahydrofuranyl-N-succinimidyl carbonate (IIa), substantially free of (R)-3-tetrahydrofuranyl-succinimidyl carbonate (IIb). Compound (IIb) is referred to as "intermediate R-isomer impurity" herein.

The term "substantially free" (S)-3-tetrahydrofuranyl-N-succinimidyl carbonate (IIa) refers to compound (IIa) with less than 0.2%, preferably less than 0.15%, more preferably less than 0.1%, area percentage of HPLC of intermediate R-isomer impurity.

The process for preparation of fosamprenavir calcium (Ia) of present invention is as depicted in scheme 5.

Scheme 5: Process for preparation of fosamprenavir calcium (Ia) of the present invention.
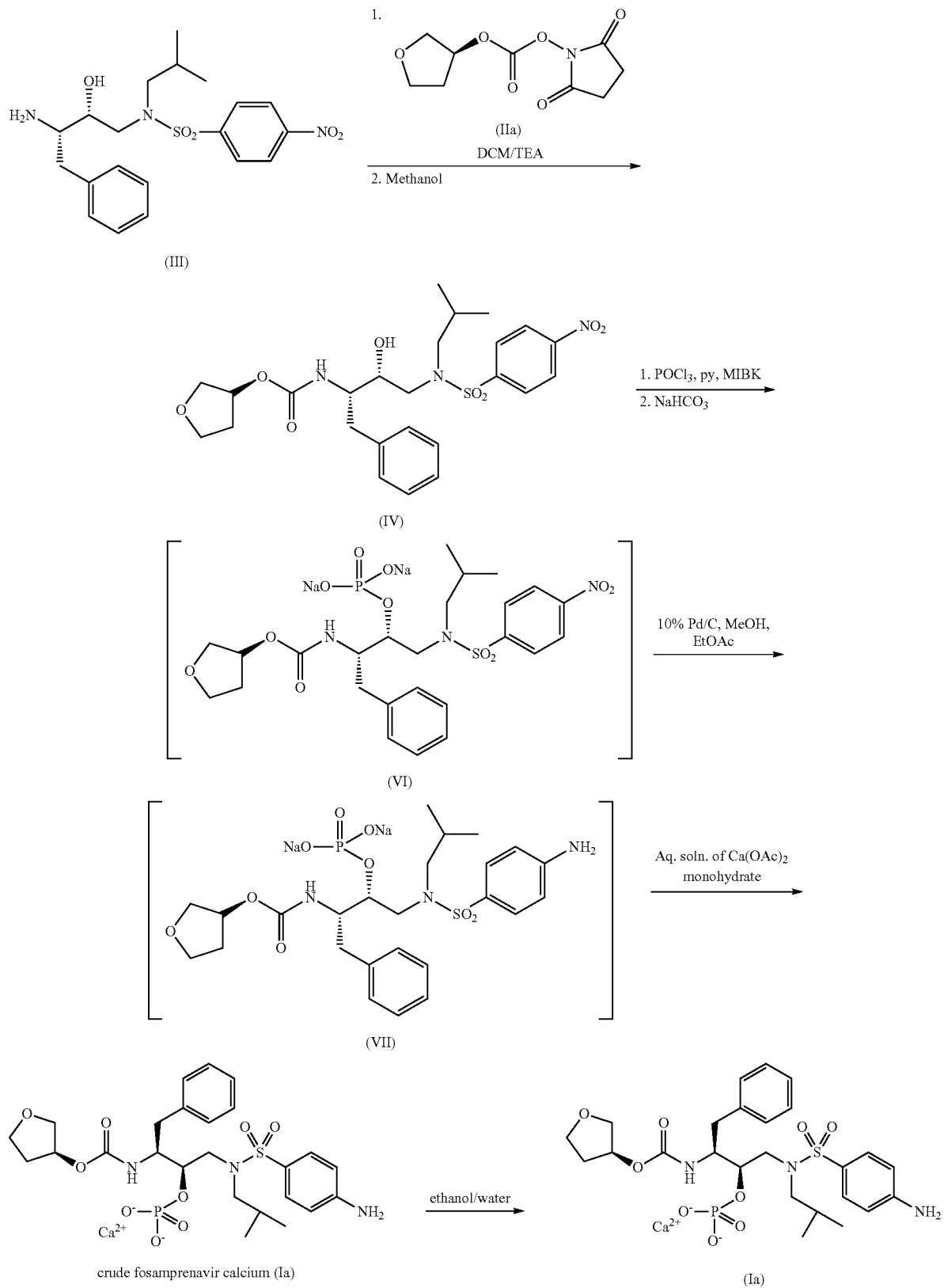

In the present invention, substantially pure (S)-3-tetrahydrofuranyl-N-succinimidyl carbonate (IIa) reacts with (2R,3S)—N-(3-amino-2-hydroxy-4-phenylbutyl)-N-isobutyl-4-nitrobenzene sulphonamide (III) to synthesize fosamprenavir calcium (Ia) substantially free of R-isomer impurity.

Samples of (S)-3-tetrahydrofuranyl-N-succinimidyl carbonate (IIa) were analyzed by HPLC to determine the content of intermediate R-isomer impurity (IIb) and samples of compound (IIa) containing intermediate R-isomer impurity less than 0.2% were selected for further reaction.

The said samples of (S)-3-tetrahydrofuranyl-N-succinimidyl carbonate (IIa) containing intermediate R-isomer less than 0.2% were used for reaction with (2R,3S)—N-(3-amino-2-hydroxy-4-phenylbutyl)-N-isobutyl-4-nitrobenzene sulphonamide (III) to give compound (3S)-tetrahydro-3-furanyl N-[(1S,2R)-1-benzyl-2-hydroxy-3-(N-isobutyl-4-nitrobenzene sulphonamido)propyl]carbamate (IV), which is converted to fosamprenavir calcium substantially free of R-isomer impurity.

The crystalline fosamprenavir calcium is then converted to amorphous fosamprenavir calcium by methods described in our earlier patent application, 277/KOL/2010 dated Mar. 18, 2010, filed at the Indian Patent Office.

Process for preparation of (S)-3-tetrahydrofuranyl-N-succinimidyl carbonate (IIa) substantially free of (R)-3-tetrahydrofuranylsuccinimidyl carbonate (IIb) comprises isolating (S)-3-tetrahydrofuranyl-N-succinimidyl carbonate (IIa) from an organic solvent selected from alcohol such as methanol, ethanol, isopropanol, tert-butyl alcohol and mixtures thereof, preferably isopropanol.

Crystallization can be carried out in an alcohol, wherein a mixture of (S)-3-tetrahydrofuranyl-N-succinimidyl carbonate (IIa) and alcohol are heated to reflux and further cooled to ambient temperature. The process wherein ambient temperature is referred to as 20-30° C.

In the present invention, manufacture of compound of formula (IIa) and fosmaprenavir calcium (Ia) has the following advantages:
a. Provides fosmaprenavir calcium (Ia) substantially free of its R-isomeric impurity (Ib);
b. It is simple and does not involve tedious and laborious techniques like column chromatography;
c. Process is easy to operate on plant scale.

The present invention is further illustrated by the following representative examples and does not limit the scope of the invention.

EXAMPLES

Details of HPLC methods for analysis are provided below:

| Variables | (S)-3-tetrahydrofuranyl-N-succinimidyl carbonate | Fosamprenavir calcium |
| --- | --- | --- |
| Column: | Chiral Pak-IA (4.6 × 250 mm) 5 μm or similar | Chiral Pak-AD-H (4.6 × 250 mm) 5 μm or similar |
| Detector: | UV detector at 210 nm | UV detector at 265 nm |
| Column temp.: | Ambient | Ambient |
| Buffer: | Not applicable | Not applicable |
| Mobile phase: | Homogeneous mixture of Ethanol, Isopropyl alcohol and Trifluoro acetic acid (55:45:0.1) | Homogeneous mixture of n-Heptane n-Butanol, n-propanol and Trifluoro acetic acid (80:18:02:0.3) |
| Sample preparation: | Mixture of tetrahydrofuran, ethanol, isopropyl alcohol and trifluoro acetic acid (7.5 mg/ml) | Homogeneous mixture of methanol, n-Heptane n-Butanol, n-propanol and Trifluoro acetic acid (1 mg/ml) |
| Injection volume: | 20 μl | 20 μl |
| Mode of elution: | Isocratic | Isocratic |
| Flow: | 0.5 ml/min | 0.8 ml/min |
| Run time: | 35 mins | 40 mins |

Example 1

(S)-3-tetrahydrofuranyl-N-succinimidyl carbonate (II)

Mixture of 800 g (3.11 mol) N,N-disuccinimidyl carbonate (IX), 200 g (2.27 mol) (S)-3-hydroxy tetrahydrofuran (VIII) and 170.36 g (2.1 mol) pyridine in 1200 ml of dichloromethane was stirred at reflux temperature for 4-5 hours. The reaction mass was filtered and the filtrate was washed with water and concentrated. To the concentrate was added 1600 ml isopropanol and stirred at 70-72° C., the reaction mass cooled, filtered, washed with isopropanol. To the wet solid was added 2888 ml isopropanol, and stirred at 70-72° C., the reaction mass cooled, filtered, washed with isopropanol and solid was dried. Yield: 311 g (60%); HPLC purity: compound (IIa): 99.92%; intermediate R-isomer impurity (IIb): 0.08%.

Example 2

Preparation of Pure Fosamprenavir Calcium (I)

Mixture of 100 g (0.23 mol) (2R,3S)—N-(3-amino-2-hydroxy-4-phenylbutyl)-N-isobutyl-4-nitrobenzene sulphonamide (III), 65 g (0.28 mol) (S)-3-tetrahydrofuranyl-N-succinimidyl carbonate (IIa) (of Example 1) and 24 g (0.23) triethylamine in 800 ml dichloromethane was stirred at ambient temperature for 4 hours, extracted with 10% sodium bicarbonate solution. The organic layer was separated, washed with water and concentrated. To the concentrated mass was added 1000 ml methanol and heated to 60-65°, cooled to 25° C. and solid was filtered, washed with methanol and dried.

Mixture of 100 g (0.186 mol) (3S)-tetrahydro-3-furyl N-[(1S,2R)-1-benzyl-2-hydroxy-3-(N-isobutyl-4-nitrobenzene sulphonamido)propyl]carbamate (IV) and 200 ml pyridine was cooled to 0-10° C. and 70.0 g (0.456 mol) of $POCl_3$ was added and stirred at ambient temperature for 4 hours, 400 ml methyl isobutyl ketone was added, cooled and 1:1 conc. HCl-water was added. Mixture was heated to 50° C. for 1 hour, cooled to 25-30° C. Organic layer was separated, washed with water and partially concentrated; 500 ml water and 31.5 g sodium bicarbonate was added and stirred. The organic layer was separated and 100 ml ethylacetate, 400 ml methanol and 5.0 g Pd/C was added. The reaction mass was stirred under hydrogen pressure for 4 hours at 30° C. The mixture was filtered, catalyst washed with methanol. The filtrate was heated to 50° C. and 33.0 g (0.186 mol) calcium acetate monohydrate in 100 ml water was added and stirred for 30 minutes. Cooled to 30° C. and stirred. Solid was filtered, washed with 1:1 mixture of methanol-water and dried to obtain crude fosamprenavir calcium.

65 g (0.104 mol) crude fosamprenavir calcium and 1170 ml denatured ethanol was heated to 70-72° C., charcaolized. Water (138 ml) was added and mixture stirred for 30 minutes. Cooled to ambient temperature and stirred. Solid filtered, washed with 1:1 ethanol-water and dried. Methanol (315 ml)

was added to the solid, stirred and filtered. The filtrate was concentrated under vacuum to obtain solid, which was dried to obtain 37.5 g pure fosamprenavir calcium. HPLC purity: fosamprenavir calcium (Ia): 99.85%; R-isomer impurity (Ib): 0.05%; all other individual impurities less than 0.1%.

The invention claimed is:

1. A process for preparation of fosamprenavir calcium (Ia) substantially free of R-isomer impurity (Ib) comprising:

(Ia)

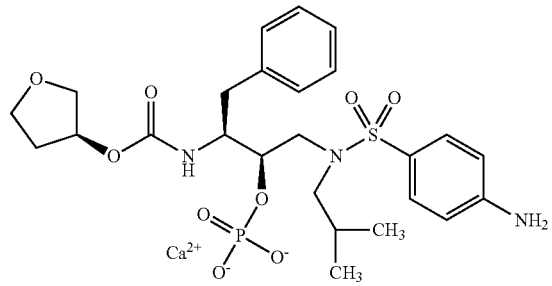

(Ib)

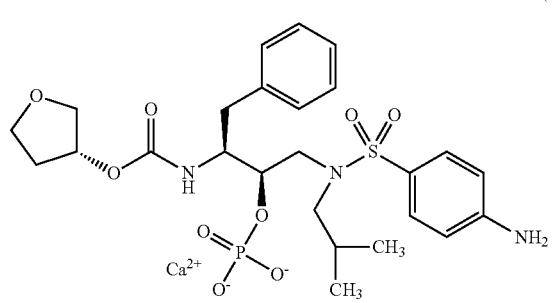

a) analyzing the level of intermediate R-isomer impurity (IIb) in a sample of (S)-3-tetrahydrofuranyl-N-succinimidyl carbonate (IIa);

(IIa)

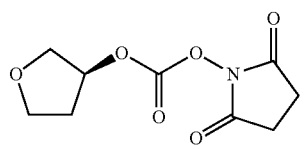

(IIb)

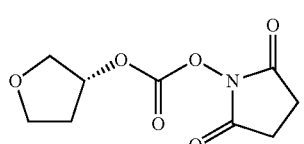

b) selecting a sample of (S)-3-tetrahydro furanyl-N-succinimidyl carbonate (IIa) containing less than 0.2% area percentage of HPLC of intermediate R-isomer impurity (IIb);

c) reacting said (S)-3-tetrahydrofuranyl-N-succinimidyl carbonate (IIa) with (2R,3S)—N-(3-amino-2-hydroxy-4-phenylbutyl)-N-isobutyl-4-nitrobenzene sulphonamide (III) to obtain (3S)-tetrahydro-3-furanyl N-[(1S, 2R)-1-benzyl-2-hydroxy-3-(N-isobutyl-4-nitrobenzene sulphonamido)propyl]carbamate (IV); and (III)

(IV)

d) conversion of compound (IV) to fosamprenavir calcium (Ia).

2. The process according to claim 1, wherein level of intermediate R-isomer impurity (IIb) is less than 0.2% area percentage of HPLC.

3. The process according to claim 1, wherein level of intermediate R-isomer impurity (IIb) is less than 0.15% area percentage of HPLC.

4. The process according to claim 1, wherein level of intermediate R-isomer impurity (IIb) is less than 0.1% area percentage of HPLC.

5. The process according to claim 1, wherein fosamprenavir calcium (Ia) contains less than 0.2% area percentage of HPLC of R-isomer impurity.

6. The process according to claim 1, wherein fosamprenavir calcium (Ia) contains less than 0.15% area percentage of HPLC of R-isomer impurity.

7. The process according to claim 1, wherein fosamprenavir calcium (Ia) contains less than 0.1% area percentage of HPLC of R-isomer impurity.

* * * * *